(12) United States Patent
Maritan

(10) Patent No.: US 8,500,693 B2
(45) Date of Patent: Aug. 6, 2013

(54) AUTOINJECTOR RECEIVED IN EXTERNAL SOCKET

(75) Inventor: Lionel Maritan, Pierre Chatel (FR)

(73) Assignee: Becton Dickinson France, Le Pont de Claix (FR)

( * ) Notice: Subject to any disclaimer, the term of this patent is extended or adjusted under 35 U.S.C. 154(b) by 234 days.

(21) Appl. No.: 12/679,812

(22) PCT Filed: Sep. 25, 2007

(86) PCT No.: PCT/IB2007/003982
§ 371 (c)(1),
(2), (4) Date: Jun. 24, 2010

(87) PCT Pub. No.: WO2009/040604
PCT Pub. Date: Apr. 2, 2009

(65) Prior Publication Data
US 2010/0256570 A1    Oct. 7, 2010

(51) Int. Cl.
*A61M 5/20* (2006.01)

(52) U.S. Cl.
USPC ........... 604/137; 604/131; 604/134; 604/136; 604/218; 604/220; 604/228; 604/229; 604/110; 604/130; 604/192; 604/198; 604/135; 604/138; 604/157; 604/207; 604/208; 604/209; 604/210; 604/211; 604/197; 600/1; 600/2; 600/3; 600/4; 600/5; 600/6; 600/7; 600/8

(58) Field of Classification Search
USPC ................. 600/1–8; 604/131, 137, 134, 136, 604/218, 220, 228, 229, 110, 130, 192, 198, 604/135, 156, 138, 157, 186, 207–211, 201, 604/197, 263

See application file for complete search history.

(56) References Cited

U.S. PATENT DOCUMENTS

| | | | | |
|---|---|---|---|---|
| 4,894,055 A | * | 1/1990 | Sudnak | 604/198 |
| 5,019,051 A | * | 5/1991 | Hake | 604/198 |
| 5,176,643 A | * | 1/1993 | Kramer et al. | 604/135 |
| 5,429,611 A | * | 7/1995 | Rait | 604/197 |
| 5,779,677 A | * | 7/1998 | Frezza | 604/134 |
| 6,162,198 A | * | 12/2000 | Coffey et al. | 604/198 |
| 6,679,864 B2 | * | 1/2004 | Gagnieux et al. | 604/198 |

(Continued)

FOREIGN PATENT DOCUMENTS

| | | |
|---|---|---|
| WO | 02/47746 A1 | 6/2002 |
| WO | WO 2004093946 A1 * | 11/2004 |
| WO | 2007/036676 A | 4/2007 |

*Primary Examiner* — Nicholas Lucchesi
*Assistant Examiner* — Scott Medway
(74) *Attorney, Agent, or Firm* — Hoffmann & Baron, LLP

(57) ABSTRACT

The present invention relates to a device for automatic injection of a product, comprising:
- a body (3) housing a container, the container being movable relative to said body between an initial position, to an insertion position;
- a safety shield (26) movable with respect to said container and said body between an insertion position to a protection position, when the user removes the device from an injection site;
- an external socket (48) receiving the body and provided with selection means (53) which can be placed by a user:
  - either in a first position, in which the body (3) and the external socket (48) are bound to each other, the safety shield extending beyond the distal end of both said body and said external socket in the protection position;
  - or in a second position, in which the external socket (48) is able to move axially in the distal direction with respect to the body (3), both the safety shield and the external socket extending beyond the distal end of said body, in the protection position.

8 Claims, 3 Drawing Sheets

U.S. PATENT DOCUMENTS

| | | | |
|---|---|---|---|
| 6,830,560 B1* | 12/2004 | Gross et al. | 604/143 |
| 7,033,343 B2* | 4/2006 | McWethy et al. | 604/506 |
| 7,442,185 B2* | 10/2008 | Amark et al. | 604/137 |
| 7,452,324 B2* | 11/2008 | Besing | 600/5 |
| 7,828,778 B2* | 11/2010 | Liversidge | 604/198 |
| 7,905,352 B2* | 3/2011 | Wyrick | 206/365 |
| 7,927,303 B2* | 4/2011 | Wyrick | 604/117 |
| 8,048,035 B2* | 11/2011 | Mesa et al. | 604/192 |
| 2001/0037087 A1* | 11/2001 | Knauer | 604/137 |
| 2002/0193746 A1* | 12/2002 | Chevallier | 604/197 |
| 2003/0050607 A1* | 3/2003 | Gagnieux et al. | 604/198 |
| 2005/0101919 A1 | 5/2005 | Brunnberg | |
| 2006/0189938 A1 | 8/2006 | Hommann et al. | |
| 2006/0195061 A1* | 8/2006 | Besing | 604/110 |
| 2006/0276756 A1* | 12/2006 | Francavilla | 604/198 |

\* cited by examiner

AUTOINJECTOR RECEIVED IN EXTERNAL SOCKET

The present invention relates to a device for automatic injection of a product in a very safe way, especially for self-injection.

In this application, the device has a longitudinal axis which is the main axis of the constitutive parts of said device. The distal end of a component or of a device is to be understood as meaning the end furthest from the user's hand and the proximal end is to be understood as meaning the end closest to the user's hand. Likewise, in this application, the "distal direction" is to be understood as meaning the direction of injection, and the "proximal direction" is to be understood as meaning the opposite direction to the direction of injection.

Some illnesses necessitate regular injections of drugs or products, for instance on a daily basis. In order to simplify the treatment, some self-injectors have been provided in order to allow the patient to perform the injection on its own.

Of course, since the patient is usually neither a nurse nor an educated person in medical devices, such self-injectors must prove to be very simple to use and also very safe. In particular, the insertion of the needle must be performed at the right depth, the correct dose of product must be injected, that is to say a complete injection must be performed, and the injector must be deactivated after use before it is disposed of. Preferably, the needle should not be exposed, before and after use, in order to prevent any accidental needlestick injury.

In order to prevent needlestick injury after use of the injection device, it has been proposed to provide the injection device with a sleeve which is in a retracted position during the injection and which extends over the needle when the user removes the device from the injection site after completion of the injection. An alternative solution is to have an injection device supported by a housing within which the needle automatically retracts at the end of injection, without the need for the user to remove the device from the injection site.

Nevertheless, depending on its apprehension of the injection operation, each patient may have different feelings about the step of neutralization of the needle at the end of injection, and some may prefer to have a sleeve that deploys over the needle when they remove the device from their skin while others may prefer that the needle automatically retracts within the device so that they do not see the needle.

In consequence, there is a need for self-injection devices that would allow the end user to choose whether he wishes that the needle automatically retracts within the device at the end of injection without having to remove the device from the injection site or on the contrary whether he prefers to remove the device at the end of injection so as to trigger the extension of a sleeve for covering the needle.

The present invention meets this need by proposing a device for automatic injection of a product into an injection site, said device comprising means allowing the end-user to choose how the neutralization of the needle at the end of injection occurs.

The present invention relates to a device for automatic injection of a product into an injection site, said device having a longitudinal axis and comprising:
- a body capable of housing a container, the container being movable relative to said body between an initial position, in which a tip of a needle provided on the container does not extend beyond a distal end of said body, to an insertion position, distally spaced relative to said initial position and in which the tip of the needle extends beyond said distal end of said body;
- a safety shield arranged inside the body and receiving at least partially the container, the safety shield being automatically movable with respect to the container and said body between an insertion position, in which the tip of the needle extends beyond a distal end of said safety shield, to a protection position, when the user has removed the device from the injection site, in which the safety shield extends beyond the distal end of said body over a length enough so that the tip of the needle does not extend beyond a distal end of said safety shield;

characterized in that said device further comprises:
- an external socket receiving the body, having open proximal and distal ends, said distal end of the external socket lying substantially in the same plane as the distal end of the body, in the insertion position;
- a selection means provided on the external socket, and being movable with respect to said external socket, where said selection means can be placed by a user:
  - either in a first position, in which the body and the external socket are bound to each other in the axial direction, so that, in the protection position, the safety shield extends beyond the distal end of both said body and said external socket;
  - or in a second position, in which the external socket is able to move axially in the distal direction with respect to the body, the device being designed so that, in the protection position, both the safety shield and the external socket extend beyond the distal end of said body, substantially over the same length.

The removal of the device from the injection site by a user causes the automatic extension of the safety shield out of the distal end of the body, in order to cover and protect the needle. This function is already performed in prior art devices.

Thanks to the arrangement according to the invention, when the selection means are placed in the first position, the removal of the device from the injection site entails the axial movement of the safety shield in the distal direction with respect to the body. Since the external socket and the body are mutually axially linked, the user sees the safety shield extending beyond the distal end of the external socket or, in other words, the external socket moving up, together with the body placed inside it, with respect to the safety shield. For the user, such a functioning is similar to the functioning of some known devices, except that the body is located inside an additional external socket.

Moreover, when the selection means are placed in the second position, the removal of the device from the injection site still entails the axial movement of the safety shield, with respect to the body, in the distal direction. In other words, the body moves axially, in the proximal direction, with respect to the safety shield. However, since the external socket is no longer bound to the body in the axial direction, this movement of the body does not cause a movement of the external socket, with respect to the safety shield. Consequently, the movement occurring within the device is a proximal displacement of the body outside the safety shield and inside the external socket; said safety shield and said external socket do not move one with respect to the other. The user sees no component extending beyond the distal end of the device, and can consider the needle has retracted inside the device.

Therefore, the invention makes it possible for the user to choose whether he prefers the needle to be covered by a component (the safety shield) extending around it, or to retract inside the device, once the injection has been completed. This double function is achieved through a selection means which is very simple to manipulate. Furthermore, to achieve this goal, it is not necessary to provide two separate devices, depending on the user's choice. It is neither required to make use of complicated means: an additional socket placed outside the body of an existing device, provided with selection means, makes it possible to shift from one needle protection method to another.

In an embodiment, the selection means have a first part which extends at least partially outside the socket so that it can be handled by a user, and a second part which extends at least partially inside the socket and which is designed to cooperate with a corresponding means provided on the body, when the selection means are in the first position, in order to bind the body and the external socket at least in one axial direction.

For example, the free end of the second part of the selection means is designed to abut onto a shoulder provided on said body, in order to prevent an axial displacement of the socket with respect to the body in the distal direction.

The selection means may comprise a lever housed in a window provided in the external socket, the lever being able to swivel on a swiveling axis with respect to the external socket. Preferably, the swiveling axis of the selection means lies in a plane substantially orthogonal to the longitudinal axis and substantially tangential to the external socket.

In an embodiment, the external socket and the body have corresponding shoulders that mutually cooperate, at least in the insertion position, in order to prevent an axial displacement of the socket with respect to the body in the proximal direction. With this arrangement, and when the selection means are placed in the first position with their second part abutting onto a shoulder provided on the body, the external socket and the body can not move axially one with respect to the other, in either direction.

The socket may further comprise a stop provided on its internal face, able to abut onto a shoulder arranged on said body, in the protection position and when the selection means are in the second position, in order to prevent further axial displacement of the body in the proximal direction with respect to the socket.

Preferably, the external socket has substantially the same length as the body, the proximal and distal ends of the external socket lying substantially in the same plane as the proximal and distal ends of the body, respectively, in the insertion position.

In an embodiment, the movement of the safety shield between the insertion and the protection position is automatically caused by elastic means which are arranged between the safety shield and the container and which expands when the user removes the device from the injection site.

The device of the invention will now be further described in reference to the following description and attached drawings in which.

Figure 1:
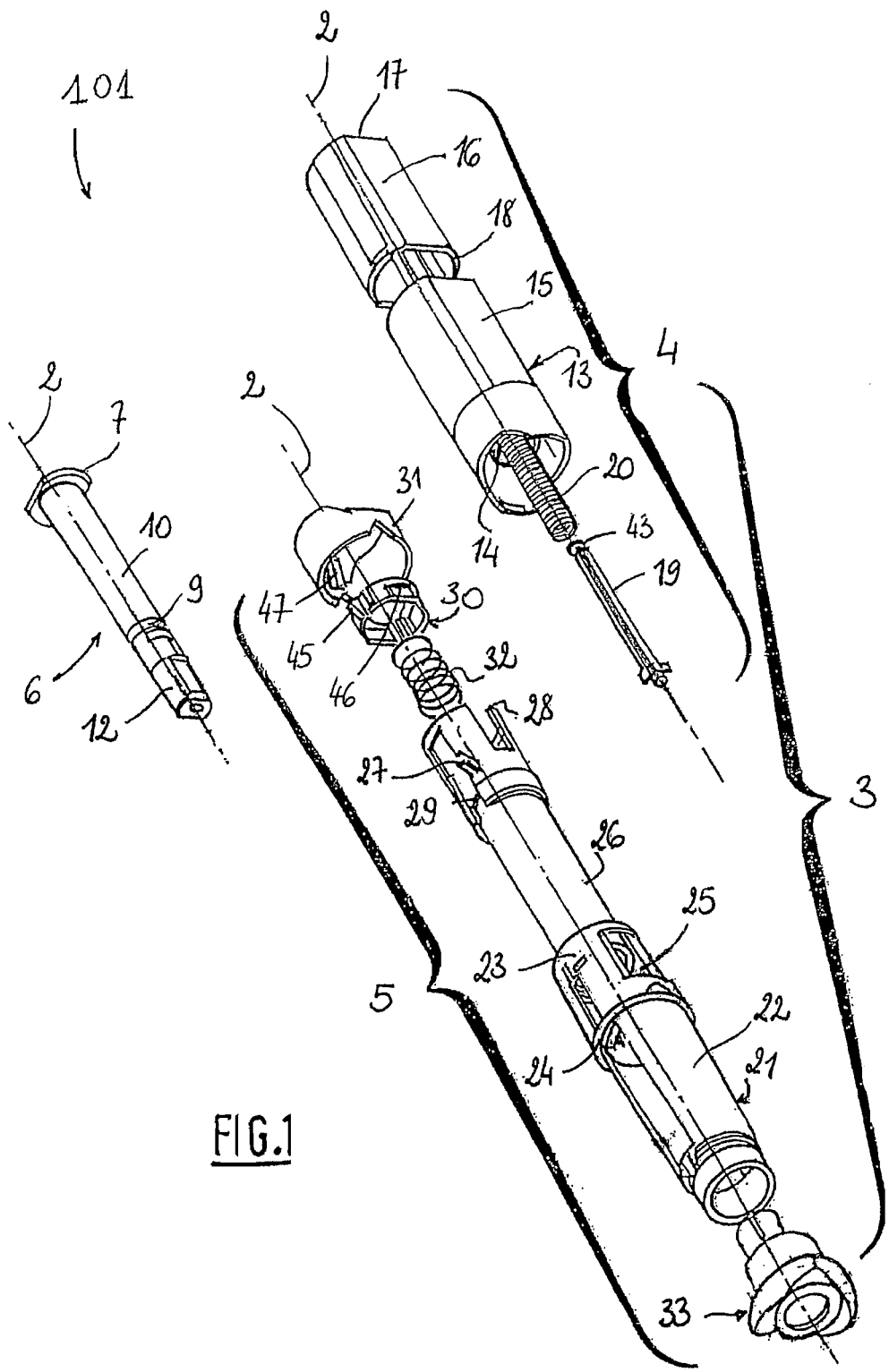
FIG. 1 is a partial exploded perspective view of an embodiment of the device of the invention.
Figure 2:
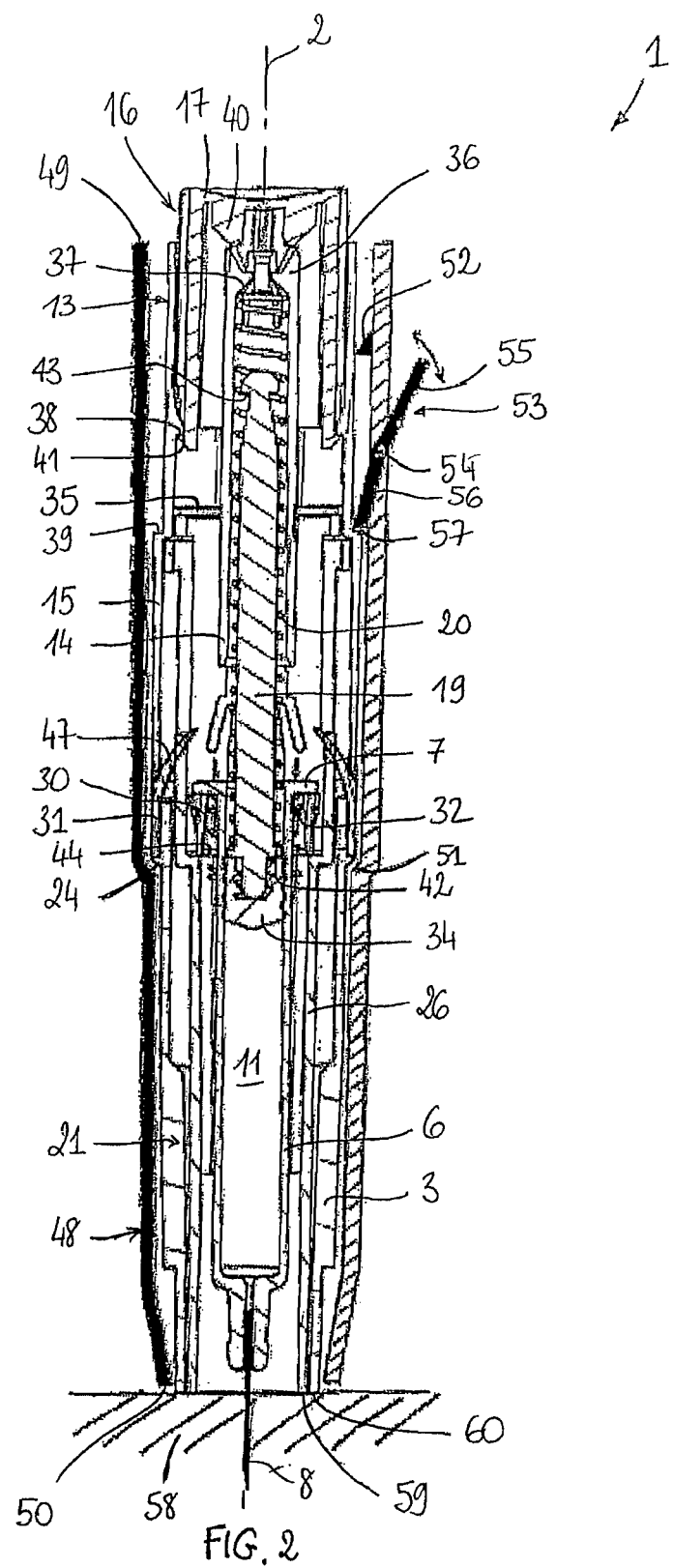
FIG. 2 is a longitudinal cross section of the device of the invention, placed against a user's skin at an injection site, with the container in its insertion position before injection.
Figure 3:
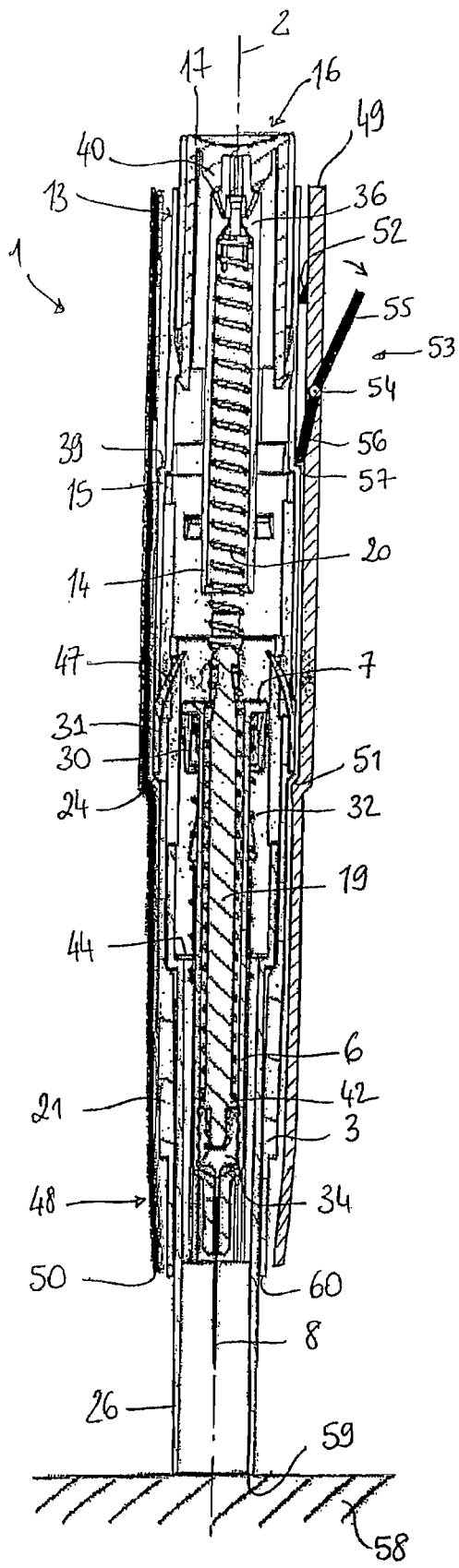
FIG. 3 is a longitudinal cross section of the device of FIG. 2, after the injection, with the selection means in the first position, in order to cause the deployment of the sleeve.
Figure 4:
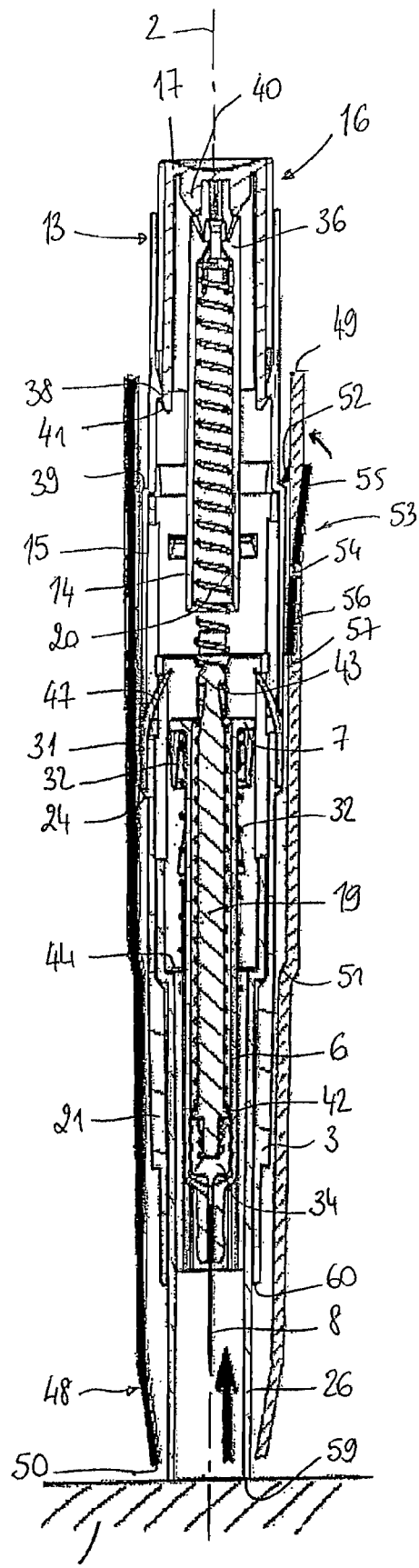
FIG. 4 is a longitudinal cross section of the device of FIG. 2, after the injection, with the selection means in the second position, in order to cause the retraction of the needle.

Referring now to the drawings, the present invention will now be described in detail. FIG. 1 shows an exploded perspective view of a part of a device for automatic injection according to an embodiment of the present invention and generally designated by reference number 1. Actually, FIG. 1 shows an injection device 101 which is to form part of the device 1 for automatic injection of the invention of FIGS. 2-4. The device 1 for automatic injection of the invention of FIGS. 2-4 comprises the injection device 101 as shown on FIG. 1 received within an external socket 48 (see FIGS. 2-3). The device 1 has a longitudinal axis 2 which is the main axis of the constitutive parts of said device, as described below. It is generally made of plastics.

The device 1 comprises a body 3 comprised of an upper body assembly 4 and a lower body assembly 5 that may be connected to each other by means of a snap-fit connection, screw-type connection, bayonet connection, or other means of connecting two parts together, in an unreleasable way or not.

A container 6 such as, for example, a syringe, is received in the body 3, the container 6 being movable axially relative to said body 3. Preferably, the container 6 is partially received in each of the upper and lower body assemblies 4, 5. The container 6 has a flange 7 defined at an open proximal end, and an injection needle 8 (see FIG. 2) at a substantially closed distal end 9. Lateral walls 10 extend between the proximal and distal ends and define a reservoir 11 sized and shaped to contain a predetermined amount of a product for injection. The injection needle 8 is in fluid communication with the reservoir 11 and provides an outlet port of the container 6 for the product.

A needle shield 12 is provided at the distal end of the container 6 to cover and protect the needle 8 before use of the device 1. The needle shield 12, which is generally made of natural or synthetic rubber material, also provides for a sealing means of the distal end of the container 6 before use. A piston 34 (see FIG. 2) provided in the container 6 is movable within the reservoir 11, with respect to the container 6. The movement of the piston causes the product to be expelled from said container 6 through the needle 8 during the injection of the product into the patient.

The body 3 illustrated in FIG. 1 is only one possible embodiment of a body of a device according to the invention, and will be now briefly described.

The upper body assembly 4 has a generally cylindrically shaped outer sleeve 13 comprised of an inner cylinder 14 and an outer cylinder 15, the cylinders 14, 15 being linked to each other by at least a radial wall 35. The proximal end of the inner cylinder 14 is provided with two flexible teeth 36, capable of being radially deflected, and with an inner radial rim 37. The outer cylinder 15 comprises an inner radial rim 38 and, distally spaced from said inner radial rim 38, a shoulder 39 forming a radial surface on the external face of said outer cylinder 15.

A push button 16, received in the outer sleeve 13, has a proximal end closed by a transversal wall 17 which forms a pushing surface for the user to exert a manual pressure on said push button 16, and a distal open end 18. The distal face of the transversal wall 17 comprises two distal teeth 40, and the distal open end 18 is provided with an outer radial rim 41 designed to cooperate with the inner radial rim 38 of the outer cylinder 15 of the upper body assembly 4 in the insertion position (see FIG. 2).

A plunger rod 19 for causing the piston to move with respect to the container 6 is received within the inner cylinder 14 of said outer sleeve 13 of the upper body assembly 4. The plunger rod is provided at its distal end with a flange 42 and at its proximal end with a radial stop 43.

A first spring 20 is provided between said plunger rod 19 and said inner cylinder 14: the distal end of the spring 20 bears on the flange 42 of the plunger rod 19, and the proximal end of the spring 20 bears on the distal face of the inner radial rim 37 of the inner cylinder 14. Spring 20 causes displacement of the container 6 within the body 3 from an initial position, in which a tip of the needle 8 does not extend beyond the distal end of the body 3 to an injection position (FIG. 2), distally spaced relative to said initial position and in which the tip of the needle 8 extends beyond said distal end of said body 3 and is exposed over a predetermined length. Spring 20 further causes movement of the piston within the container 6 to cause the product to be expelled therefrom through the needle 8.

The lower body assembly 5 comprises a housing 21 which receives at least partially the container 6. The container 6 is movable relative to said housing 21 between an initial position, in which a tip of the needle 8 does not extend beyond a distal end of the housing 21, and an insertion position, distally spaced relative to said initial position and in which the tip of the needle 8 extends beyond the distal end of the housing 21 and is exposed over a predetermined length (see FIG. 2).

The housing 21 has a general cylindrical shape and is open at both ends. The housing 21 has a distal part 22 and a proximal part 23 of greater diameter, joined by a radial wall 24. Two opposite windows 25 are provided in the proximal part 23 of housing 21.

The lower body assembly 5 also includes a safety shield 26 that is at least partially received within the housing 21. A proximal part of the safety shield 26 is provided on its outer wall with two opposite flexible tongues 27 capable of being radially deflected. The proximal part of the safety shield 26 is also provided with two opposite first proximal teeth 28 and with two opposite second proximal teeth 29, distally spaced from said first proximal teeth 28. The safety shield 26 is provided, on its inner wall, with a radial rim 44, distally spaced from said flexible tongues 27.

The safety shield 26 is coupled to the housing 21 and is able to move between a first position and a second position in which the tip of the needle does not extend beyond a distal end of the safety shield 26.

The device 1 further comprises an inner ring 30 which receives part of the proximal portion of said container 6, the inner diameter of said inner ring 30 being less than the outer diameter of the flange 7 of said container 6 so as to prevent the container 6 from passing completely through the ring 30 when ring 30 and container 6 are assembled together. When assembled together, the inner ring 30 and container 6 may move together within the upper and lower body assemblies 4, 5 as the container 6 is moved from its initial position to its insertion position. The inner ring 30 comprises at least two distal legs 45 and at least two outer radial rims 46, tangentially spaced from said two distal legs 45.

The device 1 also comprises an outer ring 31 which receives, at least partially, said inner ring 30. The outer ring 31 is provided on its inner wall with at least two opposite radially flexible tongs 47 that extend in the proximal direction.

A second spring 32 is provided between container 6 and inner ring 30. As shown on FIG. 2, the distal end of the second spring 32 bears on the proximal face of the radial rim 44 of the safety shield 26, and the proximal end of said second spring 32 bears on a distal face of said inner ring 30.

The device 1 of the present invention can also be provided with a deshielder 33 which carries the needle shield 12. Prior to use of the device 1, a user removes the deshielder 33, which also removes the needle shield 12.

Finally, the device 1 comprises an external socket 48 which is substantially cylindrical, with open proximal and distal ends 49, 50. The external socket 48 receives the body 3 and has substantially the same length, the external socket 48 being arranged so that the body cannot be seen by a user, at least in the initial and insertion positions (see FIG. 2).

The external socket 48 has a shoulder 51 which is designed to cooperate with the radial wall 24 of the housing 21, at least in the insertion position (FIG. 2), in order to prevent an axial displacement of the socket 48 with respect to the housing 21 in the proximal direction. The external socket 48 also comprises a stop 52 on its internal face, close to its proximal end 49, and a window, which is distally spaced from the stop 52.

In the window is housed a lever 53 which can swivel, with respect to the external socket 48, about an axis 54. The axis 54 lies in a plane substantially orthogonal to the device axis 2 and substantially tangential to the external socket 48, said swiveling axis 54 being arranged substantially in the center of the lever 53. Said lever 53 act as a selection means, as will be explained later.

The lever 53 comprises a first part 55 which extends in the proximal direction, at least partially outside the socket 48, and a second part 56 which extends in the distal direction, at least partially inside the socket 48, and which has a free end 57.

Initially, the lever 53 is placed in a first position (as in FIGS. 2 and 3), where the first part 55 substantially entirely extends outside the socket 48 and can be caught by a user. In this first position, the free end 57 of the second part 56 is in abutment onto shoulder 39 of the outer cylinder 15 of the body 3, in order to prevent an axial displacement of the socket 48 with respect to the body 3 in the distal direction. Because of the additional cooperation between the radial wall 24 of the body and the shoulder 51 of the external socket 48, the body 3 and the external socket 48 are bound to each other axially in both directions.

From the first position, and after the end of the injection, a user can push the first part 55 of the lever 53, in order to place lever 53 in the second position (FIG. 4), where the lever 53 is substantially parallel to the device axis 2. In this position, the lever 53 is nearly entirely housed in the window: its first part 55 and second part 56 does not extend outside, respectively inside, the external socket 48. Consequently, the free end 57 of the second part 56 no longer cooperates with shoulder 39 of the outer cylinder 15 of the body 3, and the body 3 is thus free to move axially in the proximal direction with respect to the external socket 48.

The general functioning of the device 1 will now be briefly explained. Some more details can be found in PCT/IB2007/002016.

The device 1 is provided to a user ready-to-use, the container 6 being filled with a predetermined dose of an injectable product.

Before use of the device 1, the container 6 is held in its initial position in which the tip of the needle 8 does not extend beyond the distal end of the body 3. The first spring 20 is held in a compressed condition by flexible teeth 36 of the inner cylinder 14 being engaged in the radial stop 43 of the plunger rod 19 and the flexible tongues 47 of the outer ring 31 being engaged in the radial rim 46 of the inner ring 30. The inner ring 30 and thus the container 6 are thereby prevented from moving distally. The inner ring 30 is also prevented from moving proximally by the proximal part 23 of the housing 21.

Furthermore, the flexible tongues 27 of the safety shield 26 are engaged on an abutment surface of the housing 21, and the second spring 32 is in non-compressed or extended condition.

The flange 7 of the container 6 bears on the inner ring 30. The container 6 is therefore retained in its initial position by the combined actions of the flexible teeth 36 of the inner cylinder 14, the radial stop 43 of the plunger rod 19 and the inner ring 30.

Prior to use, the user removes the deshielder 33 and the needle shield 12 and places the device 1 against his/her skin at an injection site 58. Then, the container 6 is still retained in its initial position, and the needle 8 is still protected by the safety shield 26.

The push button 16 is in a passive state such that depression by a user on the pushing surface 17 will not cause the device 1 to make an injection. Indeed, the movement of the push button 16 in the distal direction is possible but limited by retaining means (not described) which guarantee that the device 1 can not be triggered or activated at this stage, for safety reasons.

The triggering of the device 1 of the invention requires at least two steps.

In a first step, the user applies the device 1 on the injection site 58 by means of the bearing surface 59 of the safety shield 26, which initially extends slightly further in the distal direction with respect to the distal end 60 of the housing 21. The safety shield 26 is then caused to move relative to said housing 21 in the proximal direction, until the bearing surface 59 and the distal end 60 lie substantially in the same plane (as in FIG. 2).

This movement makes it possible to deactivate the retaining means of the push button 16, which is then in an active state. Furthermore, the container 6 is also placed in an active state, since the movement of the safety shield 26 has caused the flexible tongues 47 of the outer ring 31 to deflect radially (thanks to the second proximal teeth 29 of the safety shield 26), and thereby to disengage from the radial rim 46 of the inner ring 30. Although being in its active state, the container 6 is retained in its initial position and can move to its injection position, in the distal direction, only if the push button 16 is pressed.

In a second step, the user can trigger the device 1 to start the automatic injection, by pressing manually the push button 16, in the distal direction. Consequently, the teeth 40 of the push button 16 come in contact with the flexible teeth 36 of the inner cylinder 14 and make them deflect radially and outwardly. Since the flexible teeth 36 are now disengaged from the radial stop 43 of the plunger rod 19, the first spring 20 is now free to expand, and it pushes distally the plunger rod 19, the container 6 and the inner ring 30 to the injection position. Consequently, the needle 8 pierces the user's skin (position illustrated in FIG. 2) and the injectable product is then automatically expelled from the container 6 into the user's skin, by means of the expansion of the first spring 20.

During this insertion of the needle 8, the inner ring 30 has moved distally and its distal legs 45 have come in contact with the flexible tongues 27 of the safety shield 26, causing them to be deflected radially and inwardly. Moreover, the second spring 32 has been caused to compress. Yet, the distal end of said second spring 32 bears on the radial rim 44 of said safety shield 26 which is maintained against the injection site 58 by the distal pressure exerted by the user on the device 1 and said second spring 32 is therefore not free to expand.

Once the injection is complete, the user removes the device 1 from the injection site 58. This automatically causes the safety shield 26 to move distally with respect to the body 3 (being moved away from the container 6 and body 3 thanks to the expansion of the second spring 32), i.e. to extend from the housing 21 and to cover and protect the needle 8. In other words, the body 3 moves in the proximal direction with respect to the safety shield 26. In this protection position, the safety shield 26 may be locked against proximal movement, thereby preventing unintended access to the contaminated needle 8.

The removal of the device 1 from the injection site 58 causes other relative movements of the various components of the device 1, which movements depend on the position of the lever 53.

If the lever is in the first position (FIG. 3), as explained above, the body 3 and the external socket 48 are axially bound to each other, in both directions.

As a consequence, the external socket 48, as the body 3, moves in the proximal direction with respect to the safety shield 26. The proximal and distal ends 49, 50 of the external socket 48 remains substantially in the same plane as the proximal and distal ends of the body 3, respectively. Therefore, in the protection position, the safety shield 26 extends beyond the distal end of both said body 3 and said external socket 48. For the user, the visual effect is similar to a conventional device where the safety shield expands to cover the needle.

If the lever is in the second position (FIG. 4), as explained above, the body 3 is free to move axially in the proximal direction with respect to the external socket 48.

As a consequence, when the body 3 moves in the proximal direction with respect to the safety shield 26, the external socket 48 is not caused to move similarly. Therefore, in the protection position, the safety shield 26 extends beyond the distal end of said body 3 but remains substantially in the same plane as the distal end of the external socket 48. For the user, the visual effect is the following: the needle has retracted in the proximal direction within the device. It should be noted that, in the protection position, the stop 52 provided on the external socket 48 is designed to abut onto the shoulder 39 of the outer cylinder 15, in order to prevent the further axial displacement of the body 3 in the proximal direction with respect to the socket 48.

The device of the invention makes it possible for the user to choose between two protection methods of the contaminated needle after the injection step, in a very simple way since it is just necessary to push a small lever.

Furthermore, this inventive device does not require a great modification of existing devices provided with an expanding safety shield: the existing device only has to be placed into an additional external socket provided with the appropriate selection means.

Advantageously, and notably to avoid misuses (such as an accidental activation of the retraction, by placing the lever in the second position, before the end of injection), the lever can be judiciously placed, enough protected from untimely handling, and clearly identified.

In case the user forgets to push the lever and then removes the device from the injection site, the needle will all the same be protected because of the automatic deployment of the safety shield. Consequently, the device of the invention remains as safe as known devices.

The invention claimed is:

1. A device for automatic injection of a product into an injection site, said device having a longitudinal axis and comprising:
    a body capable of housing a container, the container being movable relative to said body between an initial position, in which a tip of a needle provided on the container does not extend beyond a distal end of said body, to an insertion position, distally spaced relative to said initial position and in which the tip of the needle extends beyond said distal end of said body;
    a safety shield arranged inside the body and receiving at least partially the container, the safety shield being automatically movable with respect to the container and said body between an insertion position, in which the tip of the needle extends beyond a distal end of said safety shield, to a protection position, when the user has removed the device from the injection site, in which the safety shield extends beyond the distal end of said body over a length enough so that the tip of the needle does not extend beyond a distal end of said safety shield;

an external socket receiving the body, having open proximal and distal ends, said distal end of the external socket lying substantially in the same plane as the distal end of the body, in the insertion position, said external socket defining an inwardly extending shoulder configured to interferingly engage a portion of said body upon a predetermined extent of proximal movement of said external socket relative to said body, said interfering engagement preventing further proximal movement of said external socket relative to said body;

a selection means provided on the external socket, and being movable with respect to said external socket, where said selection means can be placed by a user:

either in a first position, in which the body and the external socket are bound to each other in the axial direction, so that, in the protection position, the safety shield extends beyond the distal end of both said body and said external socket;

or in a second position, in which the body is able to move axially in the proximal direction with respect to the safety shield, the device being designed so that, in the protection position, both the safety shield and the external socket extend beyond the distal end of said body, substantially over the same length.

2. Device according to claim 1, characterized in that the selection means have a first part which extends at least partially outside the socket so that it can be handled by a user, and a second part which extends at least partially inside the socket and which is designed to cooperate with a corresponding means provided on the body, when the selection means are in the first position, in order to bind the body and the external socket at least in one axial direction.

3. Device according to claim 2, characterized in that the free end of the second part of the selection means is designed to abut onto a shoulder provided on said body, in order to prevent an axial displacement of the socket with respect to the body in the distal direction.

4. Device according to claim 1, characterized in that the selection means comprise a lever housed in a window provided in the external socket being able to swivel on a swiveling axis with respect to the external socket.

5. Device according to claim 4, characterized in that the swiveling axis of the selection means lies in a plane substantially orthogonal to the longitudinal axis and substantially tangential to the external socket.

6. Device according to claim 1, characterized in that the socket comprises a stop provided on its internal face, able to abut onto a shoulder arranged on said body, in the protection position and when the selection means are in the second position, in order to prevent further axial displacement of the body in the proximal direction with respect to the socket.

7. Device according to claim 1, characterized in that the external socket has substantially the same length as the body, the proximal and distal ends of the external socket lying substantially in the same plane as the proximal and distal ends of the body, respectively, in the insertion position.

8. Device according to claim 1, characterized in that the movement of the safety shield between the insertion and the protection position is automatically caused by elastic means which are arranged between the safety shield and the container and which expands when the user removes the device from the injection site.

\* \* \* \* \*

UNITED STATES PATENT AND TRADEMARK OFFICE
CERTIFICATE OF CORRECTION

PATENT NO.        : 8,500,693 B2                                              Page 1 of 1
APPLICATION NO. : 12/679812
DATED             : August 6, 2013
INVENTOR(S)       : Lionel Maritan It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 417 days.

Signed and Sealed this
Fifteenth Day of September, 2015

Michelle K. Lee
*Director of the United States Patent and Trademark Office*